United States Patent [19]

Fujii et al.

[11] Patent Number: 5,726,163
[45] Date of Patent: Mar. 10, 1998

[54] DERMATOLOGIC COMPOSITION

[75] Inventors: Takako Fujii; Kazuo Hasegawa; Shigeo Tanaka; Fumio Urushizaki, all of Tokyo, Japan

[73] Assignee: Taisho Pharmaceutical Co., Ltd., Tokyo, Japan

[21] Appl. No.: 676,253

[22] PCT Filed: Jan. 19, 1995

[86] PCT No.: PCT/JP95/00045

§ 371 Date: Jul. 17, 1996

§ 102(e) Date: Jul. 17, 1996

[87] PCT Pub. No.: WO95/19762

PCT Pub. Date: Jul. 27, 1995

[30] Foreign Application Priority Data

Jan. 19, 1994 [JP] Japan ............................. 6-4255

[51] Int. Cl.$^6$ .................. A61K 31/685; A61K 31/66; A61K 31/575; A61K 31/045

[52] U.S. Cl. .................. 514/78; 514/103; 514/171; 514/738

[58] Field of Search .................. 514/78, 171, 738, 514/103

[56] References Cited

FOREIGN PATENT DOCUMENTS

| 63-51311 | 3/1988 | Japan . |
| 5-39485 | 2/1993 | Japan . |
| 5-70323 | 3/1993 | Japan . |

OTHER PUBLICATIONS

Influence of Phospholipids Purity and Polyols on the Temperature Dependence of the Permeability of Liposomes, Kuni arakane et al, J.Soc. Cosmet. Chem. Japan, vol. 25, No. 3 1991, pp. 171–177.

Remington's Pharmaceutical Sciences, Fifteenth Ed., Mack Publishing Co., p. 1249 (1975).

*Primary Examiner*—Phyllis G. Spivack
*Attorney, Agent, or Firm*—Cushman Darby & Cushman IP Group of Pillsbury Madison & Sutro LLP

[57] ABSTRACT

A dermatologic composition is disclosed which comprises a hydrogenated phospholipid having an iodine value of 10 or less and a phosphatidylcholine content of 90% or more, a cholesterol and an oily ingredient.

1 Claim, No Drawings

DERMATOLOGIC COMPOSITION

This application claims benefit of international application PCT/JP 95/00045, filed Jan. 19, 1995.

TECHNICAL FIELD

The present invention relates to a dermatologic composition whose barrier property on the skin surface has been heightened by mixing a specific phospholipid, a cholesterol, a diol having a molecular weight of 430 or less and an oily ingredient.

BACKGROUND ART

In the rough skin or dry skin, the barrier function of stratum corneum deteriorates, thereby resulting in an increase of the transepidermal water loss (hereinafter, referred to as "TEWL"). Also in the case of patients suffering from atopic dermatitis which is a disease attracting much attention in recent days, the barrier function of stratum corneum deteriorates, thereby increasing the TEWL.

To improve the above-described state, it has been the conventional practice to apply a plugging type base material such as vaseline which inhibits TEWL. In this case, however, the plugging type base material has uncomfortable touch feeling such as oiliness and stickiness so that it involves a problem in feeling upon use.

DISCLOSURE OF THE INVENTION

As a result of an extensive investigation, the present inventors have paid attention to the fact that a specific phospholipid not only has strong resistance to oxidation but also is colorless and odorless, and is stable with the passage of time. It has been found that a dermatologic composition, which can inhibit TEWL, is free from discoloration and odor, and has excellent feeling upon use, can be obtained by using the above specific phospholipid in combination with a cholesterol, a diol having a molecular weight of 430 or less and an oily ingredient, thus completing the invention.

The present invention therefore provides a dermatologic composition which comprises a hydrogenated phospholipid having an iodine value of 10 or less and a phosphatidylcholine content of 90% or more (hereinafter, referred to as "specific phospholipid"), a cholesterol, a diol having a molecular weight of 430 or less and an oily ingredient.

As a source for the specific phospholipid suitable for use in the present invention, any one of soybean, yolk, synthetic products and semisynthetic products can be used. The specific phospholipid is added in an amount of from 0.01 wt % to 30 wt % based on the total amount of the composition.

The cholesterol is added at a ratio ranging from 1:0.01 to 1:50 relative to the specific phospholipid. Outside the above range, the advantage of the present invention cannot be obtained.

The diol having a molecular weight of 430 or less is employed to improve the compatibility of the specific phospholipid with other ingredients, thereby providing a composition having good emulsion stability. Examples of the diol include 1,3-butylene glycol, propylene glycol and dipropylene glycol. They may be used either singly or in combination. They are added in an amount of from 0.1 wt % to 10 wt % based on the total amount of the composition.

Examples of the oily ingredient include vegetable oils such as olive oil, avocado oil and castor oil; animal oils such as beef tallow, turtle oil, mink oil and horse oil; semisynthetic or synthetic oils or fats such as hydrogenated beef tallow, glyceryl triisooctanoate and hydrogenated horse oil; vegetable ester oils such as carnauba wax, candelilla wax and jojoba oil, animal-vegetable ester oils such as beeswax, lanolin and whale oil; synthetic ester oils such as cetyl isooctanoate, isopropyl myristate, octyldodecyl myristate, neopentyl glycol dicaprate and cholesterol hydroxy stearate; hydrocarbons such as liquid paraffin, paraffin, microcrystalline wax, ceresin and squalane; synthetic oils such as liquid polyisobutylene and silicone oil; and oil-soluble vitamins such as vitamin E acetate and vitamin A oil. Of these oily ingredients, oils in the form of liquid are preferred, with neopentyl glycol dicaprate, squalane and silicone oil being most preferred. The above oily ingredient is added at a ratio of from 1:1 to 1:100 relative to the phospholipid. Outside the above range, the target composition cannot be obtained. Incidentally, the above oily ingredients can be used either singly or in combination.

The dermatologic composition according to the present invention can be used as cosmetics, quasi-drug or drug in the form of cream, milky lotion, lotion, bathing agent or the like. At this time, it is possible to add one or more ingredients generally employed for cream, milky lotion, lotion or bathing agent within an extent not damaging the advantage of the present invention.

Examples of such ingredients include higher fatty acids (for example, myristic acid, palmitic acid, stearic acid, isostearic acid and oleic acid), higher alcohols (for example, myristyl alcohol, cetyl alcohol, stearyl alcohol, oleyl alcohol, 2-hexyldecanol and 2-octyldodecanol), thickeners (for example, carboxyvinyl polymer), plugging type base materials (for example, vaseline), antiseptics (for example, parabens such as methyl paraben), nonionic surfactants (for example, sorbitan fatty acid ester, polyoxyethylene sorbitan fatty acid ester, glycerin fatty acid ester, polyglycerin fatty acid ester, polyethylene glycol fatty acid ester, polyoxyethylene alkyl ether, polyoxyethylene polyoxypropylene alkyl ether and polyoxyethylene hydrogenated castor oil derivative), ionic surfactants (for example, alkylphosphate ester salt, N-acylglutamate salt and benzalconium chloride), neutralizing agents in the case where a carboxyvinyl polymer is used as a thickener (for example, sodium hydroxide, potassium hydroxide, triethanol amines and basic amino acids (such as arginine and lysine)) and water-soluble vitamins.

The dermatologic composition according to the present invention may be prepared by an ordinary method. It is however preferred to conduct fine pulverization in a high-pressure homogenizer to obtain a composition having excellent stability. When a carboxyvinyl polymer is added, on the other hand, it is preferred to obtain the composition by mixing an emulsified phospholipid in a neutralized gel.

INDUSTRIAL APPLICABILITY

The present invention has made it possible to provide a dermatologic composition which has high TEWL inhibitory effects, is colorless and odorless and is excellent as a preparation (in other words, is excellent in feeling upon use).

BEST MODE FOR CARRYING OUT THE INVENTION

The present invention is now illustrated in greater detail with reference to the following Inventive Examples and Test Examples. Incidentally, in the Inventive Examples and Test Examples, the term "PC content" as used herein means a phosphatidylcholine content.

Inventive Example 1

| Ingredient | Amount added (g) |
| --- | --- |
| (Ingredient A) | |
| Squalane | 20 |
| Hydrogenated soybean phospholipid having an iodine value of 3.4 and a PC content of 98% | 4 |
| Cetanol | 1.0 |
| Stearyl alcohol | 1.0 |
| Cholesterol | 6 |
| Cholesterol hydroxy stearate | 4 |
| Palmitic acid | 2 |
| Stearic acid | 2 |
| Silicone 5 CS | 10 |
| Propylene glycol | 10 |
| (Ingredient B) | |
| Methyl paraben | 0.6 |
| L-arginine | 1.0 |
| Glycerin | 20 |
| Purified water | Balance to give 200 g in total |

The ingredients A and B were heated together at 80° C., followed by emulsification in a homogenizer. The thus obtained emulsion was cooled down to room temperature to give a cream.

Inventive Example 2

| Ingredient | Amount added (g) |
| --- | --- |
| (Ingredient A) | |
| Squalane | 15 |
| Hydrogenated soybean phospholipid having an iodine value of 3.4 and a PC content of 98% | 6 |
| Vitamin E acetate | 3 |
| Cholesterol | 1.5 |
| Cholesterol hydroxy stearate | 1.5 |
| Stearic acid | 1.5 |
| Silicone 5 CS | 15 |
| 1,3-butylene glycol | 15 |
| (Ingredient B) | |
| Methyl paraben | 0.9 |
| Glycerin | 30 |
| (Ingredient C) | |
| Carboxyvinyl polymer | 0.9 |
| L-arginine | 1.5 |
| Purified water | Balance to give 300 g in total |

The ingredients A and B were dissolved in a portion of the purified water, followed by heating at 80° C. and emulsification in a high-pressure homogenizer ("MANTON GAULIN"; manufactured by GAULIN Corporation). The thus obtained emulsion was mixed with a gel prepared from the ingredient C and the remaining portion of the purified water. The resulting mixture was further mixed in a homomixer, followed by cooling to room temperature to give a milky lotion.

Inventive Example 3

| Ingredient | Amount added (g) |
| --- | --- |
| (Ingredient A) | |
| Squalane | 1.0 |
| Hydrogenated soybean phospholipid having an iodine value of 3.4 and a PC content of 98% | 1.0 |
| 1,3-butylene glycol | 3.0 |
| Cholesterol | 0.5 |
| (Ingredient B) | |
| Glycerin | 30 |
| Polyoxyethylene(5) Sodium cetyletherphosphate | 0.15 |
| Purified water | Balance to give 300 g in total |

The ingredient A was dissolved at 80° C. The ingredient B which had been heated in advance was added to the resulting solution, followed by mixing in a high pressure homomixer to give a lotion.

Inventive Example 4

| Ingredient | Amount added (g) |
| --- | --- |
| (Ingredient A) | |
| Squalane | 5.0 |
| Hydrogenated soybean phospholipid having an iodine value of 3.4 and a PC content of 98% | 1.0 |
| 1,3-butylene glycol | 10 |
| Cholesterol | 0.5 |
| Stearic acid | 0.5 |
| Vitamin E acetate | 1 |
| (Ingredient B) | |
| Glycerin | 10 |
| Methyl paraben | 0.3 |
| Purified water | balance |
| (Ingredient C) | |
| Carboxyvinyl polymer | 0.25 |
| Arginine | 0.3 |
| Purified water | Balance to give 100 g in total |

The ingredient A was dissolved at 80° C. The ingredient B which had been heated in advance was added to the resulting solution, followed by mixing in a high pressure homomixer. The resulting mixture was added to a gel which had been prepared from the ingredient C in advance, followed by mixing to give a milky lotion.

Comparative Examples 1–6

In each of Comparative Examples 1–6, a milky lotion was prepared in the same manner as in Inventive Example 4 except that 1 g of the phospholipid shown in Table 1 was used instead of 1 g of the hydrogenated soybean phospholipid having an iodine value of 3.4 and a phosphatidylcholine content of 98%.

TABLE 1

| Comparative Example No. | Iodine Value | PC Content |
| --- | --- | --- |
| 1 | 106 | 90 or more |
| 2 | 3.7 | 65–75 |
| 3 | 97.4 | 65–75 |
| 4 | 22.0 | 25–35 |
| 5 | 4.2 | 15–25 |
| 6 | 80 | 15–25 |

Test Example 1

Hairless rats were employed for the test in groups, each group consisting of three rats. After the abdominal skin of each of the rats was epilated, the 4.5 cm$^2$ portion of the epilated skin was subjected to degreasing treatment three times with 3 ml of a 1:1 acetone and ether mixture solution, whereby a "rough skin model" was prepared. To the rough skin model, each sample shown in Table 2 was applied in an amount of 20 μl. Six hours after the application, the TEWL value was measured by an evaporimeter. Incidentally, each sample in Table 2 was prepared by heating each ingredient to about 80° C. and then emulsifying them in a high-pressure homogenizer ("MANTON GAULIN"). For reference, TEWL values of a degreasing-treatment-free group (untreated group) and a group (control) which had been subjected to degreasing treatment but not to the application of a sample were measured.

The results are shown in Table 3 wherein the TEWL value is an average of the group.

TABLE 2

| | Amount Added (g) | | | |
| --- | --- | --- | --- | --- |
| | Sample No. 1 | Sample No. 2 | Sample No. 3 | Sample No. 4 |
| Squalane | | | 1 | 100 |
| Phospholipid* | 1 | 1 | 1 | |
| 1,3-butylene glocol | | 3 | 3 | |
| Cholesterol | | | 0.5 | |
| Purified water | Balance to give 100 g | Balance to give 100 g | Blance to give 100 g | |

TABLE 2-continued

| | Amount Added (g) | | | |
| --- | --- | --- | --- | --- |
| | Sample No. 1 | Sample No. 2 | Sample No. 3 | Sample No. 4 |

*The term "phospholipid" used in Table 1 means hydrogenated soybean phospholipid having an iodine value of 3.4 and a PC content of 98%.

TABLE 3

| Sample No. | TEWL Value (g/m2h) |
| --- | --- |
| Control (immediately after degreasing treatment) | 98 |
| Control (6 hours after degreasing treatment) | 62 |
| Sample 1 | 40 |
| Sample 2 | 40 |
| Sample 3 | 12 |
| Sample 4 | 40 |
| Untreated | 5 |

Test Example 2

Milky lotions prepared in Inventive Example 4 and Comparative Examples 1–6 were stored at 40° C. for 6 months, and presence or absence of discoloration and odor were macroscopically judged. As a result, it was found that the milky lotion prepared in Inventive Example 4 was free from discoloration and odor, but those prepared in Comparative Examples 1–6 each changed to yellow and had an odor.

In the claims:

1. A dermatologic composition which comprises a hydrogenated phospholipid having an iodine value of 10 or less and a phosphatidylcholine content of 90% or more, a cholesterol, a diol having a molecular weight of 430 or less and an oily ingredient, in which the hydrogenated phospholipid and the cholesterol are mixed at a ratio of from 1:0.01 to 1:50, the hydrogenated phospholipid and the oily ingredient are mixed at a ratio of from 1:1 to 1:100, and the hydrogenated phospholipid is added in an amount of from 0.01 wt % to 30 wt % based on the total amount of the composition.

* * * * *